(12) United States Patent
Komatu et al.

(10) Patent No.: US 6,231,878 B1
(45) Date of Patent: May 15, 2001

(54) TREATING WATER FOR DERMATOSES IN DOMESTIC ANIMALS

(75) Inventors: Shigeru Komatu, Honjou; Tetuya Murai, Kisakata-machi, both of (JP)

(73) Assignees: Miura-denshi Kabushiki-kaisha; Toshiyuki Miura, both of Yuri-gun (JP)

( * ) Notice: Subject to any disclaimer, the term of this patent is extended or adjusted under 35 U.S.C. 154(b) by 0 days.

(21) Appl. No.: 09/225,232

(22) Filed: Jan. 4, 1999

Related U.S. Application Data (63) Continuation of application No. 08/745,247, filed on Nov. 8, 1996, now abandoned, which is a continuation of application No. 08/296,917, filed on Aug. 31, 1994, now abandoned.

(51) Int. Cl.$^7$ .................... A01N 25/00; A01N 59/08; A61L 2/02; C02F 1/461
(52) U.S. Cl. .................... 424/405; 424/661; 205/701; 205/746
(58) Field of Search .................... 424/405, 661; 205/701, 746

(56) References Cited

U.S. PATENT DOCUMENTS

| | | | |
|---|---|---|---|
| 3,616,355 | * | 10/1971 | Themy et al. .................... 204/149 |
| 4,761,208 | * | 8/1988 | Gram et al. .................... 204/95 |

FOREIGN PATENT DOCUMENTS

1752401 * 8/1992 (SU) .

* cited by examiner

Primary Examiner—Shelley A. Dodson
Assistant Examiner—Marina Lamm
(74) Attorney, Agent, or Firm—Oblon, Spivak, McClelland, Maier & Neustadt, P.C.

(57) ABSTRACT

Treating water for dermatoses in domestic animals mainly composed of acidic water obtained by electrolysis, which acidic water is highly effective in treatment of a dermatosis in a domestic animal when applied or sprayed to domestic animals several times at an initial stage of the dermatosis.

3 Claims, 3 Drawing Sheets

TREATING WATER FOR DERMATOSES IN DOMESTIC ANIMALS

This application is a Continuation (CIP) of application U.S. Ser. No. 08/745,247 filed on Nov. 8, 1996, now abandoned, which is a continuation of application U.S. Ser. No. 08/296,917, filed on Aug. 31, 1994, abandoned.

BACKGROUND OF THE INVENTION

1. Fields of the Invention

The present invention relates to treating water for a dermatosis in a domestic animal which is effective in treatment of epidermal diseases in domestic animals such as cattle and swine.

2. Descriptions of the Prior Art

Domestic animals such as cattle and swine have often suffered from dermatoses, probably because they are crowded in a limited space for their farming. Especially, in cattle farming, cattle are likely to suffer from dermatomycosis (hereinafter referred to as DM) which arises from infection of the skin with *T.verrucosum* and sometimes causes cattle to die. Similarly, in swine farming, swine are likely to suffer from an exudative epidermitis (hereinafter referred to as EE) generally called "greasy pig disease", which is caused by infection of the skin with *Staphylococcus hyicus*. In EE, exudation of blood components out of the blood vessel in the affected part sometimes causes swine to die through intracorporeal infection.

In treatment of such dermatoses, it is conventional to apply or spray proper antibacterial agents locally or systemically according to sensitivities of pathogenic bacteria of respective dermatoses.

The present inventors have found that it is highly effective in treatment of dermatoses in domestic animals to apply or spray acidic water obtained by continuous electrolysis of salt tap water several times at an initial stage, and have proposed treating water for dermatoses in domestic animals composed mainly of the acidic water obtained by continuous electrolysis of salt tap water (Japanese Patent Application No. 239099/1993).

However, antibacterial agents are not so effective in serious cases, and treatment of dermatoses with antibacterial agents often end in failure due to induction of resistance of pathogenic bacteria against the antibacterial agent.

It has been also found that as such treating water for dermatoses in domestic animals, acidic water having a pH of at most 2.6, a high oxidation-reduction potential of at least +1050 mV, a concentration of active chlorine of 15 to 30 ppm and a concentration of dissolved oxygen of 20 to 30 ppm, which is obtained by electrolysis of salt tap water, is remarkably effective in the treatment.

SUMMARY OF THE INVENTION

The present invention has been accomplished on the basis of the discovery that it is remarkably effective to apply or spray acidic water obtained by electrolysis of salt tap water onto domestic animals several times at an initial stage in treatment of dermatoses in domestic animals, and provides treating water for epidermal diseases in domestic animals composed mainly of the acidic water obtained by continuous electrolysis of salt tap water.

In the present invention, the acidic water is obtained from an anode side of an electrolytic cell by processing salt tap water at a processing rate of 1 to 2.5 I/min by means of the electrolytic device which comprises an electrolytic cell which is directly connected to a cock supplying tap water and constructed so that after a small amount of common salt (NaCl) is added to the tap water, the resulting salt tap water is dividedly introduced to an anode side and a cathode side of the electrolytic cell, an electric power unit which applies predetermined voltage and current to electrodes of the electrolytic cell, and solenoid operated directional control valves at outlets of both the anode and cathode sides, and is directly applied or sprayed onto the skin of a domestic animal as treating water for an epidermal disease in a domestic animal.

DETAILED DESCRIPTION OF THE PREFERRED EMBODIMENT

Among the acidic water thus obtained, acidic water having a pH of at most 2.6, an oxidation-reduction potential of at least +1050 mV, a concentration of active chlorine of 15 to 30 ppm and a concentration of dissolved oxygen of 20 to 30 ppm is used as the treating water.

Particularly, in 1993, the weather had been exceptionally unseasonable since the start of the year, whereby sheds had been in bad circumstances. In particular, in farms raising plural domestic animals, many cattle suffered from DM and many swine suffered from EE. Besides, DM and EE were resistant against various treating agents than usual, due to such bad shed circumstances.

In treatment of dermatoses in domestic animals with the acidic water obtained by continuous electrolysis of salt tap water, details of the treating mechanism have not been clear yet. However, it is presumed that remarkable effects of the acidic water against dermatoses in domestic animals are attributable to chlorine gas generated upon the electrolytic reaction and dissolving in the acidic water in a hydrated state. Chlorine gas has a rapid and strong bactericidal activity associated with its oxidizing power.

Namely, the reason for the remarkable effect of the acidic water against dermatoses is presumed that as being capable of oxidizing amino groups and the like on surfaces of microorganisms, chlorine has extensive antimicrobial effects against bacteria, fungi and viruses.

Although the acidic water obtained by electrolysis not only contains chlorine gas but also has an extremely low pH, its rapid and strong bactericidal effect seems to be attributable mainly to chlorine gas. Without chlorine, the acidic water lo rapidity of its bactericidal effect, although a bactericidal effect itself still remains. Therefore, it is presumed that when the acidic water obtained by electrolysis is used as treating water for dermatoses in domestic animals, an synergical action of its low pH and chlorine in it makes the acidic water effective in treatment of dermatoses in domestic animals.

Electron microscopy of *T.verrucosum* has revealed that *T.verrucosum* to which the acidic water is applied has no hyphae and that the acidic water induces morphological changes in hyphae of the bacterium. With respect to EE, it was observed that development of the dermatosis is inhibited by applying the acidic water to it at a low concentration. Because the acidic water has a low pH and contains a large amount of chlorine related substances (gaseous chlorine and hypochlorite radical), it seems that the low pH of the acidic water causes disruption of a growing environment of its pathogenic bacterium or that a cell membrane of the bacterium is changed by strong oxidation or reduction. Further, such a strong oxidation-reduction reaction can be expected from its high oxidation-reduction potential, since an oxidation-reduction potential indicates so-called susceptibility to oxidation. After all, the low pH of the acidic water and the chlorine-related substances contained therein seems to contribute its bactericidal or antibacterial effects synergistically.

Still further, in the blood test, the effect of the acidic water seems to also relate to immunity, because the lyses follow decrease in γ-GTP, GOT and $E_{OS}$ values and the higher the γ-globulin, the sooner lyses are observed. Besides, the acidic water is penetrable since it is naturally water and an affected part is washed at the same time as application of the acidic water. Thus, treatment with the treating water promotes healing of affected parts.

Figure 1:
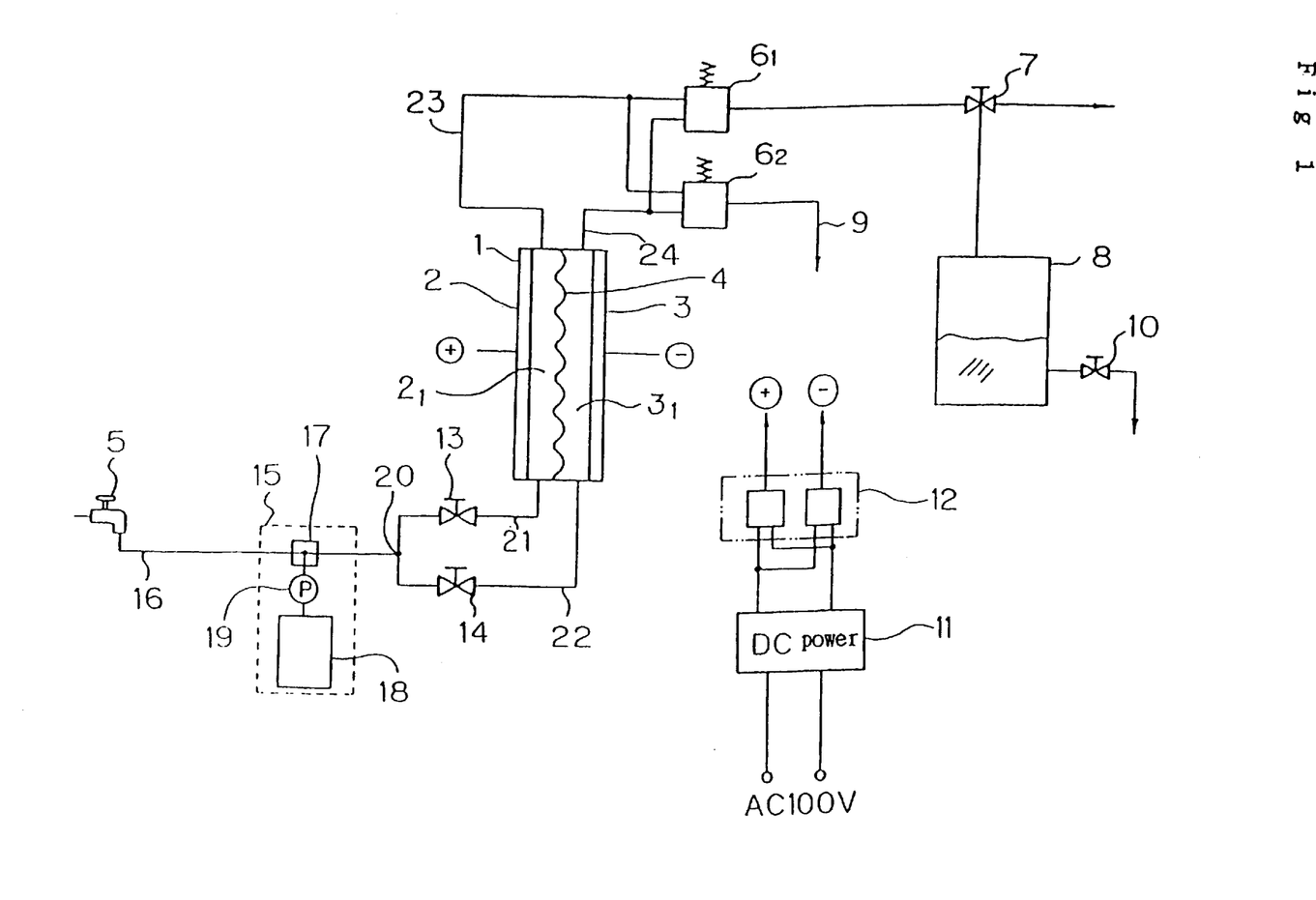
FIG. 1 is an outline of the process for producing the acidic water obtained by electrolysis to be used as the treating water for dermatoses in domestic animales of the present invention.

FIG. 1 shows an outline of the process for producing the acidic water obtained by electrolysis to be used as the treating water for dermatoses in domestic animals of the present invention. In FIG. 1, an electrolytic cell 1 is 19 cm in width, 15 cm in height and 1.25 m³ in volume. In the electrolytic cell 1, an anode 2 and a cathode 3 are provided so as to interpose an electrolytic membrane 4 between them. On one side of the electrolytic membrane 4, an anode-side region $2_1$ is provided, and on the other side a cathode-side region $3_1$. To add commercial salt to tap water, a salt-adding device 15 is provided on a pipeline 16 which connects a cock 5 supplying tap water to the anode-side region $2_1$ and the cathode-side region $3_1$, and mixes a predetermined amount of salt water to the tap water by using the principle of Venturi tube. Accordingly, the salt-adding device 15 is composed of a venturi region 17, salt water-storaging region 18 and a flow control valve for the salt water 19. The pipeline 16 extending from the salt-adding device 15 branches at a branching point 20, and its branches, pipelines 21 and 22, lead to the anode-side region $2_1$ and the cathode-side region $3_1$ of the electrolytic cell 1 through flow control valves 13 and 14, respectively. Processed water flows out from the anode-side region $2_1$ and the cathode-side region $3_1$ through pipelines 23 and 24.

A DC electric power unit 11 applies a volt direct current of 48 V and 40 A across the anode 2 and cathode 3 through a relay means 12, by using a 100 V power source of commercial frequency.

The pipelines 23 and 24 are provided with solenoid operated directional control valves $6_1$ and $6_2$ synchronized with the relay means 12, to collect a constant amount of processed water flowing out from either of the anode-side region $2_1$ and the cathode-side region $3_1$. In the electrolytic device, a reverse voltage can be applied across the electrodes to recover the electrodes from deterioration resulting from a long period of continuous operation of the electrolytic device which leads to decline of the capability of electrolysis. The solenoid operated directional control valves $6_1$ and $6_2$ permit to collect processed water from an anode region as the acidic water, even during such recovery.

The pipeline 23 in provided with a directional control valve 7 so that the acidic water can be supplied directly from the end of the pipeline 23 at the processing rate or stored in a tank 8. The tank 8 is useful in the case where a large amount of the acidic water is required at once or where the acidic water is required to be heated before use. The tank 8 is provided with a cock 10 and stored acidic water is available through the cock 10 at any time and can be used as treating water for dermatoses in domestic animals.

The electrolytic device is operated to obtain the acidic water as follows.

First, a volt direct current of 48 V and 40 A is applied across the electrodes 2 and 3 so that one of them serves as an anode and the other as a cathode. Then, tap water is supplied to the electrolytic cell at a rate of 1 to 2.5 l/ml by adjusting the cock 5.

During about 20 minute's operation, about 20 l of acidic water is produced, and it is withdrawn from the end of the pipeline 23 for immediate use, or stored in the tank 8. The acidic water thus stored in the tank 8 is available for use as treating water for dermatoses in domestic animals.

In production of the acidic water to be used in the present invention, it is preferred to reverse the direction of the current at times by using the relay means 12, to prevent a decline of the capability of the electrodes caused by a long period of continuous operation. Namely, the former anode is charged negatively, and the former cathode is charged positively. It is also preferred to switch over the solenoid operated directional control valves $6_1$ and $6_2$ at the same time, so that the acidic water flowing out from the new anode-side region, i.e. the former cathode-side region, is supplied from the end of the pipeline 23 for immediate use or collected in the tank 8 and alkaline water flowing out from the new cathode-side region, i.e. the former anode-side region is drained through a pipeline 9.

The electrolytic device thus constructed is capable of producing the acidic water at a rate of 1 to 2.5 l/min. The acidic water obtained by the process is used as the treating water for dermatoses in domestic animals such as cattle and swine.

EXAMPLE 1

With respect to DM, hairs and dander collected from the affected parts were observed by using a microscope after treated with a 10% KOH solution, and incubated in a Mycocel agar medium.

With respect to EE, specimens collected from the affected parts were aerobically incubated in an agar medium containing 5% sheep blood, a DHL agar medium and a *S.hyicus* selective medium.

To examine the effect of the treating water of the present invention, dermatoses of domestic animals were clinically treated with the treating water of the present invention. The acidic water produced by operating the electrolytic cell as shown in FIG. 1 at a processing rate of 2 l/min with aforementioned current and voltage applied to the electrodes was used as the treating water.

1) Test cattle

The following test cattle are used:

Japanese Black for breeding 13

Japanese Black for fattening 30

Holstein cows 12

Holstein calves 8

F-1 5

2) Test swine

The following test swine were used:

suckling pigs 37

Another pig was used for a postmortem examination.
3) Test period
The treatment was conducted for 4 months from April to July in 1993.
4) Place
The treatment was conducted in Akita Veterinary Cinical Training Center (Akitaken-nogyokyousaikumiairengoukai-kachikurinsho-kenshujo).
5) Method of treatment
The treating water was sprayed on the skins of each test animal 1–2 times a day, and affected parts were repeatedly wiped with gauze soaked with the treating water.

With respect to DM, together with the above-mentioned microbiological examination, blood tests were conducted on the following items at intervals of 10 to 14 days:

(1) RBC (red blood cell), (2) WBC (white blood cell), (3) HT (hematocrit), (4) differential blood-count (in this example, a percentage of cosinophil was used as a differential blood-count), (5) GOT(glutamic-oxalacetic transaminase), (6) γ-GT? γ-glutamyltransferase), (7) BUN (blood urine nitrogen), (8) CA (carbonic anhydrase), (9) TP (total protein), (10) ester ratio, (11) NEFA (non esterified fatty acid).

With respect to DM, the results of the microscopic examination demonstrated the presence of arthropores and hyphae in the test cattle, and colonies of *T.veimcosum* were detected on the Mycocel agar plates.

With respect to EE, *Staphylococcus Hyicus* was detected in the media wherein the specimens collected from the affected parts. As the result of postmortem examination of a dead pig, the presence of *Staphylococcus Hyicus* in the skin abscess, intracelial abscess, kidney and brain was confirmed, and in the brain, the same bacterium was detected solely.

The results of the blood tests revealed that values of $E_{OS}$ (%), GOT (U/L), γ-GTP W) were decreased in the test cattle (Nos.139–144) after the treatment.

periods which the cattle took to be cured, depending on their species and ages.

With respect to EE, the swine having scattered lesion were cured in about a week, and the swine having the systemic lesion were cured in 10 to 14 days, with epidermolysis observed.

EXAMPLE 2

Secondly, the clinical examination was conducted in large-scale farms which are liable to be damaged by dermatoses in domestic animals from July to September, 1993, under such bad conditions that domestic animals arc susceptible to dermatoses due to unseasonable weather.
1) Test animals and method of treatment
The test animals use in Example 2 are shown in Table 2.

TABLE 2

| | Test animals | | | |
|---|---|---|---|---|
| treatment | species | Firm | Age | number |
| Acidic | Holstein (adult) | A · B | 14~18 | 12 |
| Water | Holstein (calves) | A | 1~4 | 8 |
| | Jerseys (calves) | C | 1~6 | 14 |
| | Japanese Black (for breeding) | A · E | 8~48 | 13 |
| | Japanese Black (for fattening) | D | 14~22 | 30 |
| | F-1 (Hol × Black) | A · E | 1~4 | 5 |
| | Suckling swine | F · G | 14~30 (day) | 37 |
| Non treatment | Holstein (calves) | A | 1~4 | 3 |
| Control | F-1 hybrid cow | A | 3 | 1 |
| Alkaline water | Holstein (calves) | A | 2~3 | 2 |
| | total | | | 125 |

With respect to DM, the examination was conducted from July to September, 1993, in two farms A and B raising Holsteins, a farm C raising Jerseys and two farms D and F

TABLE 1

| | Japanese Black | | | | | | | | |
|---|---|---|---|---|---|---|---|---|---|
| | Eos (%) | | | | | | GOT (U/L) | | |
| | No. 139 | No. 140 | No. 141 | No. 142 | No. 143 | No. 144 | No. 139 | No. 140 | No. 141 |
| Befor treatment | 4 | 8 | 6 | 10 | 11 | 11 | 68.24 | 66.65 | 62.91 |
| After treatment | 4 | 13 | 2 | 4 | 4 | 5 | 59.98 | 56.24 | 61.45 |

| | GOT (U/L) | | | γ-GTP (IU) | | | | | |
|---|---|---|---|---|---|---|---|---|---|
| | No. 142 | No. 143 | No. 144 | No. 139 | No. 140 | No. 141 | No. 142 | No. 143 | No. 144 |
| Befor treatment | 54.47 | 58.97 | 61.67 | 13.65 | 13.04 | 17.06 | 17.48 | 14.58 | 15.90 |
| After treatment | 46.19 | 59.18 | 52.88 | 9.67 | 9.67 | 13.74 | 13.75 | 11.95 | 12.57 |

As a result, all the test cattle were confirmed to be suffering from DM caused by infection with *T.verrucosum*, and all the test swine were confirmed to be suffering from EE caused by infection with *Staphylococcus Hyicus*.

After the confirmation, the test animals were sprayed with the treating water 1–2 times a day, or their affected parts were wiped with gauze soaked with the treating water to examine the effect of the treating water. As a result, the test cattle were completely cured of DM in 6 to 51 days (average 24.1 days), although there were some variation in the raising Japanese Black. Each farm was large-scale, raising 40 to 220 cattle, and damaged by dermatoses due to its crowded raising circumstance.

In A farm, a 2-month old F-1 calf slightly affected by DM and two Holstein-calves of 2-months old were raised by the side of a diseased cow without any treatment and observed. For comparison, two diseased Holstein calves were treated with alkaline water having a pH of 11.3, an Eh of −900 mV and a concentration of active chlorine of 0.1 ppm, which was produced at the same time of the production of the acidic water.

With respect to EE in swine, The clinical examination was conducted on 5 litters of pigs in F and G farms. In G farm, a 25-day old dead pig was subjected to a pathologicoanatomic examination, while in F farm, 10 pregnant pigs were sprayed with the acidic water once a day to examine the preventive effect.

2) Method of treatment

The acidic water was sprayed on the parts affected by DM once or twice a day, and the parts affected by EE 2 to 3 times a day, until the sprayed parts became enough wet. Pigs affected by systemic EE were bathed in the treating water. The treating water was sprayed by using a hand sprayer or a power sprayer. In the case of the hand sprayer, 100 to 150 cc of the acidic water was sprayed over about 10 minutes with the nozzle of the sprayer kept apart from the skin by about 10 cm, namely, without any special operations, at such a spraying rate that the sprayed water dries up readily under ordinary conditions. In the case of the power sprayer, 1 to 2 l of the acidic water was sprayed over 10 minutes with the nozzle of the sprayer kept apart from the skin by about 30 cm, so that the sprayed water dries up readily.

3) Verification

It was verified that the test animals suffered from dermatoses by pathological and microbiological examinations.

Pathological examination (i) DM

The hairs and dander collected from affected parts were observed by means of an optical microscope and an electron microscope, after treated with a 10% KOH solution.

(ii) EE

A dead pig of 25 days old was anatomized for pathological observations. Microbiological examination (i) DM Dander collected from affected parts were aerobically incubated in a Mycocel agar medium (manufactured by Becton) for two weeks after microscopic observations.

(ii) EE

A) Skin specimens collected from foreheads and legs of diseased pigs and hypogastrium of a pregnant pig were aerobically incubated in an agar medium containing 5% sheep blood at 37° C. for 24 hours, and detected bacteria were identified by using an Api staph system (manufactured by Biomerieux). The isolated bacterium was observed by means of an electron microscope.

B) Specimens collected from abscess, major organs and brain of a dead pig were aerobically incubated in a Devriese's *Staphylococcus hyicus* selective medium.

4) blood test

Only 13 heads of cattle were subjected to blood tests on the following 15 items twice at an interval of 10 days:

RBC, WBC, HT, differential blood-count, GOT, γ-GTP, BUN, CA, IP, GLU, IP, TCHO, FCHO/ester ratio, NEFA.

5) Morphological observation by means of a scanning electron microscope

Morphological change in bacteria were examined by using secondary electron images obtained by means of a scanning electron microscope.

i) *T.verrucosum*

Dander collected from affected parts were soaked in the acidic water or purified water for preparation of a control sample for 40 minutes, then treated with a 10% KOH solution for 20 minutes to lyse the stratum cornenm, and observed by means of a scanning electron microscope.

ii) *S.hyicus*

*S.hyicus* was cultured in a brain heart infusion broth, and centrifugally washed and collected. The collected bacterium was divided into two, and each of them was treated with 2 cc of the acidic water or purified water for 10 minutes and subjected to electron microscopic examination.

6) Judgement of cure

When defluxion of the focus and epidermization were observed, the affected part was defined to be cured. When growth of hair was observed without palindromia, the affected part was defined to be completely cured.

1) DM

Pathemas of all the cattle were of so-called incrustation type, and the affected parts were depilated and covered with thick gray dander.

In A farm farming 40 adult Holsteins, a primigravid cow purchased from I prefecture at the beginning of March of the year served as the source of infection, and gave neighboring adult cattle, 1–2 month old calves and ET cattle (which were born as a result of embryo transfer) its dermatosis successively. The pathemas were the most terrible in their faces, colla, dorsa and nates. Whereas application of antibiotics over about a month did not make the pathemas better, application of the acidic water succeeded in almost stamping out the dermatosis in 3 weeks. The ET cattle took 51 days to be completely cured due to repetitious palindromia. On the contrary, in the control cattle which were applied with purified water, the pathema did not become better, and the lesion was extended to the heads and the eyelids in a week.

Likewise, in the cattle which were applied with alkaline water obtained from the cathode side during the production of the acidic water, the pathema did not become better. Then, the acidic water was applied to the cattle instead of the purified water or alkaline water from 11th day of the examination, and the pathema tended to be improved about a week later.

Adult Holsteins (14–18 month old) in B farm were given DM during they were farmed out to D farm. The cattle were affected mainly by their eyelids and heads, and cured by application of the acidic water in the minimum period of 11 days.

In C farm raising Jerseys, among the 70 heads of grazed cattle, 14 heads, which were mainly calves, were infected per vias natural, with the source of the infection unidentified.

In C farm, when the affected cattle were applied with the acidic water once and left for a week, the pathema did not become better. However, the acidic water was applied to the cattle several times a day for the subsequent 2 weeks, and the cattle were cured in 3 weeks.

D farm, which is a public large-scale farm raising 220 heads of cattle, targets mainly fattening cattle and takes breeding Holstein calves or embryo transfer.

In the farm, 30 heads of fatted cattle and cattle which were farmed out from B farm caught DM from fatted cattle having been kept since the previous year as the source of infection. Although it is usually effective against such a disease to apply a disinfectant, application of a disinfectant for a month is not effective in the year due to bad shed circumstances resulting from the unseasonable weather. Then, the acidic water was applied to the cattle once a day, and the cattle were cured in 28 days.

In E farm, which constantly raises at least 50 heads of cattle for the purpose of breeding Japanese Black, calves just before marketing were infected with DM from F-1 cattle (F1 hybrid born as a result of crossing) purchased from an adult livestock market as feeder ET cattle although the original one month treatment of infected cattle with an antibiotic was unsuccessful, subsequent treatment with the acidic water achieved positive result with the effected cattle.

2) EE

EE broke out in F and G farms from the end of May to the middle of June, 1993. The outbreaks of EE gave the farms such serious damages that among 40 pigs at 5 litters, 3 pigs were die of EE. At the end of March, a weanling pig of about 20 days old was infected and showed the symptoms of EE, and at the beginning of June, the infection extended even to a 5-day-old pig. The infected pigs had relative low temperatures of 39.5 to 39.8° C. and turned dark brown with the hairs on the whole bodies agglutinated with exudate from the skins. Especially, the tendency was observed that the diseased pigs in F farm had systemic eruption, whereas the pigs in G farm had eruption interspersed on the whole bodies. In either farm, although there was some variation in the symptom, the diseased pigs were relatively vigorous without any special prostration or dystithia. In both farms, treatment with penicillin was not effective. In G farm, 3 pigs died before treatment with the acidic water was started, whereas no pigs died after the treatment with the acidic water.

Then, to analyze the symptoms of DM in cattle and EE in swine, pathological examinations and microbiological examinations were conducted.

Figure 2:
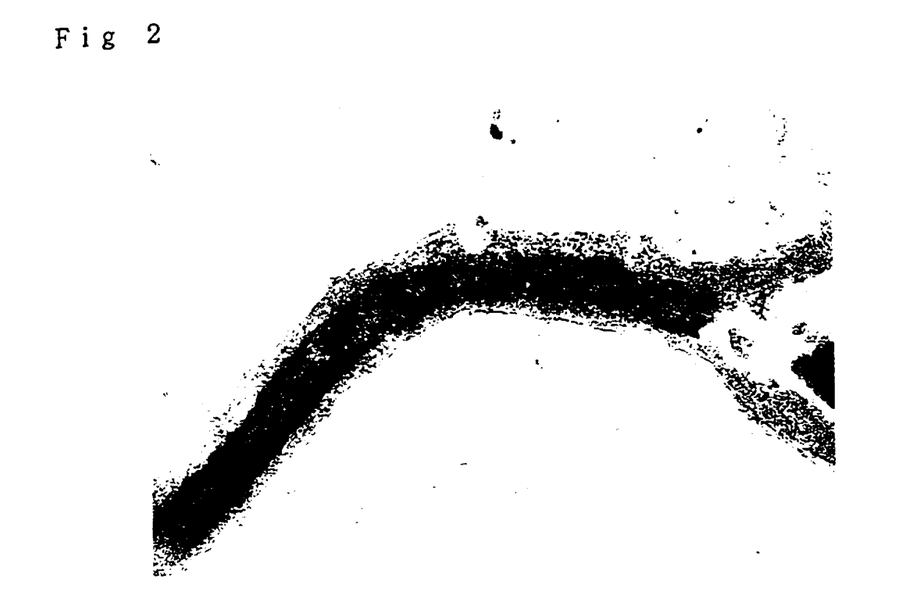
FIG. 2 is a microphtogragh of hyphae of *T.verrucosum* collected from a focus of DM.

1) Pathological examinations
  a) DM
  FIG. 2 is a microphtogragh of hyphae of spores of T.verrucosum collected from a focus of DM. As is evident from FIG. 2, arthrospore crowded around the hairs to stick them, and the hyphae were observed around the arthrospore.
  b) EE
  An infected pig of 25 days old had dark brown crusta and pisiform abscess interspersed on its surface, and parts of them showed the symptom of DM. The histological observation of the epidermis revealed that thrombosed sphacelus containing abscess was accumulated, and telangiectasia and the presence of lymphoid cells, neutrophils and the pathogenic bacterium were recognized by the observation. In the lever, ectasia of the sinusoid, activated Kupffre's cells and neutrophils were observed. With respect to other organs such as the spleen, lung, kidney and intestinum tenue, no abnormal symptoms were observed. With respect to the brain, the presence of neutrophils was recognized in the blood vessels in both the cerebral and cerebellar cortexes.

2) Microbiological examinations
  a) DM
  No strains incubated after treated with the acidic water grew.
  With respect to the control strains, the bacterium grew, forming colonies.
  b) EE
  S.hyicus was detected in the media wherein the specimens collected from the skin abscess, intracelial abscess and kidney. In the Devrise's selective medium wherein the specimen from the cerebrum, S.hyicus was detected exclusively. With respect to the other sites, S.aureus was detected predominatingly over S.hyicus.
  The strain treated with the acidic water before incubation did not grow at all.

3) Blood tests
  The statistical analyses of the difference in the average value for each test item between before and after the treatment revealed γ-GTP, GOT and $E_{OS}$ significantly decreased after the treatment with the level of significance of 5%. The averages of γ-globulin value in the Holstein calves, black breeding cattle and black fatted cattle were 2.9 g/dl, 3.42 g/dl and 1.768 g/dl, respectively. The relationship between the γ-globulin value and curing revealed that the higher the γ-globulin value, the earlier DM was cured. T-test among them revealed the significant differences among them with the level of significance of 5% or less.

4) Diagnoses
  On the basis of the clinical symptoms and the results of the examinations, these dermatoses were diagnosed as DM caused by infection with T.verrucosum or EE caused by infection with S.hyicus.

Figure 3:
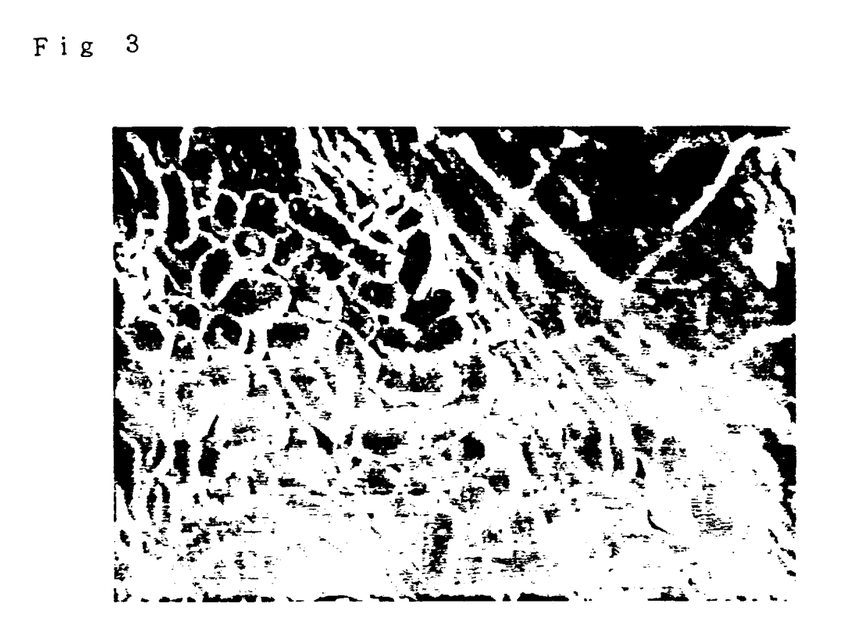
FIG. 3 is a microphotograph of the arthrospore of *T.verrucosum* after treated with the acidic water with a magnification of 2,000.
Figure 4:
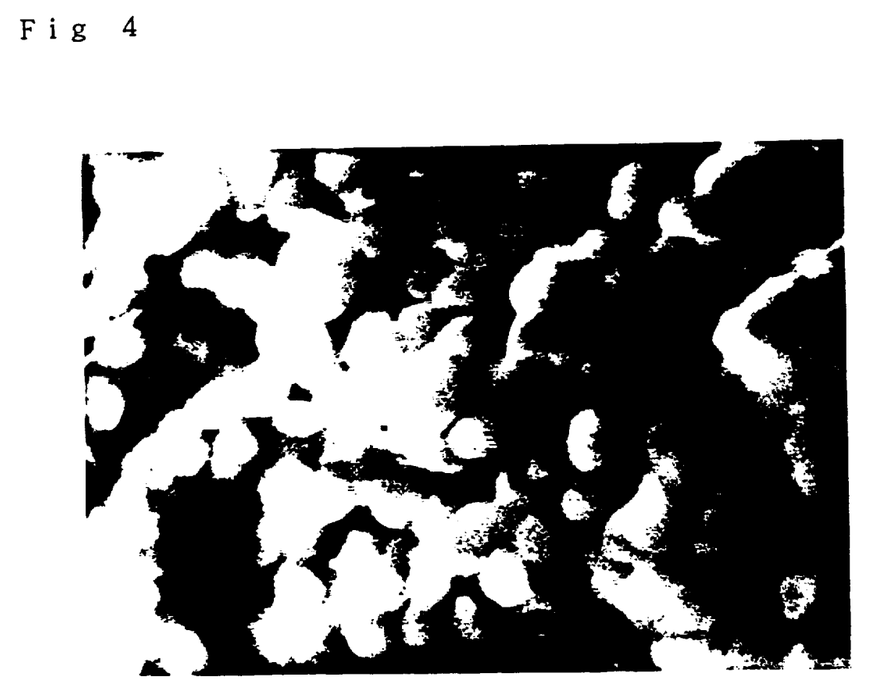
FIG. 4 is a microphotograph of *S.hyicus* after the treatment with the acidic water with a magnification of 10,000.

5) Results of the morphological observation by means of an electron microscope
  With respect to T.verrucosum not treated, both arthrospore and hyphae were observed crowdedly around the hair roots. On the other hand, with respect to the bacterium treated with the acidic water, although some arthrospore were observed, no hyphae were observed. FIG. 3 is a microphotograph of the arthrospore of T.verrucosum after treated with the acidic water with a magnification of 2,000.
  With respect to S.hyicus, although both the stains which was not treated and which was treated with the acidic water were observed with various magnifications, neither change in cell membrane such as expansion and burst nor morphological change was observed. FIG. 4 is a microphotograph of S.hyicus after the treatment with the acidic water with a magnification of 10,000.

6) Results of the treatment
  Results of the treatment were represented in Table 3 as the periods which adult Holsteins, fatted Jerseys, breeding Japanese Black, fatted Japanese Black, F-1 (F1 hybrid of Holstein with black Japanese) and suckling pigs took to be cured, respectively.

TABLE 3

| | curing period (day) | | |
|---|---|---|---|
| species | minimum | maximum | average |
| Holstein (adult) | 11 | 16 | 14.5 |
| Holstein (calves) | 6 | 21 | 16.1 |
| Jerseys (for fattening) | 10 | 32 | 21.0 |
| Japanese Black (for breeding) | 31 | 51 | 34.2 |
| Japanese Black (for fattening) | 28 | 34 | 28.6 |
| F-1 (Hol × Black) | 6 | 31 | 22.0 |
| Suckling swine | 7 | 14 | 10.5 | a) DM
  The test cattle took 6 to 51 days (average 24.1 days) to be cured of DM, although the curing period varied depending on their species and ages. The adult Holsteins required the shortest curing period, and the young Japanese Black took a considerable long period to be cured. There was a tendency that one having a serious focus took a longer period to recover from DM compared with another head of cattle of the same species and age. The ET cattle were liable to have a relapse due to their inherent valetudinarianism, took 51 days to be completely cured.
  With respect to the cattle to which purified water was applied and the cattle to which alkaline water was applied for the purpose of comparison, the symptoms got worse acceleratingly. Accordingly, these cattle were treated with the acidic water instead of the purified or alkaline water from 11th day, and after the treatment with the acidic water was started, the fatted cattle in D farm were completely cured in 28 days on the average.
  b) EE
  The swine having scattered lesion were cured in about a week, and the swine having systemic lesion were cured in 10 to 14 days, showing the epidermolysis. Among the cured pigs, no pigs grew into unthrifty pigs, or so-called runt pigs. However, it was observed that the cured pigs grew about 7 to 10 days behind sound pigs.
  To examine the preventive effect of the acidic water, 10 pregnant pigs in F farm were sprayed with the acidic water once a day until their farrowing, whereby the preventive effect of the acidic water was proved, although 3 pigs among a litter of pigs showed slight symptoms of DM at their ages of 2 weeks old.

Particularly, in a serious case or in the case where the disease makes rapid progress, a preventive measure and a prompt treatment is required, because it is difficult to manage the disease after pathopoiesis. For such a preventive measure and a prompt treatment, it is preferred to apply the acidic water to swine at least 2 times a day and to the inside and the outside of a piggery.

By applying the acidic water produced by continuous electrolysis of salt tap water of the present invention to test cattle affected by DM caused by infection with *T.verucosum* or test swine affected by EE caused by infection with Staphylococcus hyicus once or twice a day, or wiping their affected parts with gauze soaked with the acidic water and then applying the acidic water to them, the test cattle were completely cured of DM in 6 to 51 days (average 24.1 days) although the curing period varied depending on their species and the test swine having scattered lesion and those having systemic lesion were cured in about a week and in 10 to 14 days, respectively, showing the epidermolysis.

The therapeutic effect of the acidic water is comparable to those of conventional antibiotics, and since the acidic water loses its acidity and return to mere water without any special processes as time passes, the acidic water is useful as environmentally friendly treating water harmless to men and beasts.

As described above, the acidic water of the present invention has therapeutic effects against dermatoses in domestic animals, is particularly effective to 2 species of microbes having different properties, and is effective even to strains resistant against antibiotics.

As evident from the microphotograph of *T.verrucosum*, *T.verrucosum* to which the acidic water is applied has no hyphae and the acidic water induces morphological changes in hyphae of the fungus. With respect to EE, it was observed that development of the dermatosis is inhibited by applying the acidic water to it at a low concentration. Because the acidic water has a low pH and contains a large amount of chlorine related substances (gaseous chlorine and hypochlorite radical), it seems that the low pH of the acidic water causes disruption of a growing environment of *S.hyicus* or that a cell membrane of the bacterium is changed by strong oxidation or reduction. Still further, it seems that the acidic water has the therapeutic effects because it is more penetrable compared with other therapeutic agents, the application of the treating water is accompanied by washing affected parts, and that the and the therapeutic effects of the acidic water relates to immunity in the tested result.

What is claimed is:

1. A method of treating dermatosis in a domestic animal, which comprises:

directly applying or spraying an acidic electrolysis water which hag a pH of at most 2.6. an active chlorine concentration 15 to 30 ppm and a oxidation-reduction potential of at least 1050 mV, onto the skin of a domestic animal for the treatment of dermatosis.

2. The method of claim 1, wherein the acidic electrolysis water inhibits the growth of *T. verrucosum* and changes the bacterium morphologically, when applied or sprayed.

3. The method of claim 1, wherein the acidic electrolysis water causes disruption of the growing environment for *S. Hyicus,* and changes and breaks down the cell membrane of the bacterium when applied or sprayed.

* * * * *

UNITED STATES PATENT AND TRADEMARK OFFICE
CERTIFICATE OF CORRECTION

PATENT NO. : 6,231,878 B1
DATED : May 15, 2001
INVENTOR(S) : Komatsu et al.

It is certified that error appears in the above-identified patent and that said Letters Patent is hereby corrected as shown below:

<u>Title page,</u>
Items [12] and [75], the 1st Inventor's name is incorrect.
Items [12] and [75], should read:

-- [12]

United States Patent
               Komatsu et al.

[75] Inventors:    Shigeru Komatsu, Honjou; Tetuya Murai,
                     Kisakata-machi, both of [JP] --

Item [30], the Foreign Application Priority information has been omitted.
Item [30], should read:

-- [30]      Foreign Application Priority Data

Aug. 31, 1993    [JP] ...........................5-239099 --

Signed and Sealed this

Thirtieth Day of October, 2001

Attest:

NICHOLAS P. GODICI
*Attesting Officer*     *Acting Director of the United States Patent and Trademark Office*